United States Patent [19]

Suzuki et al.

[11] Patent Number: 5,158,746
[45] Date of Patent: Oct. 27, 1992

[54] APPARATUS FOR QUANTIFYING OXYGEN

[75] Inventors: Takashi Suzuki, Yokohama; Teruo Akiyama, Tokyo, both of Japan

[73] Assignee: Japan Oxygen Co., Ltd., Tokyo, Japan

[21] Appl. No.: 670,749

[22] Filed: Mar. 15, 1991

Related U.S. Application Data

[62] Division of Ser. No. 148,841, Jan. 26, 1988, Pat. No. 5,021,352.

[30] Foreign Application Priority Data

Jan. 29, 1987 [JP] Japan .................................. 62-19241

[51] Int. Cl.$^5$ .......................... G01N 21/76; G01J 1/48
[52] U.S. Cl. ........................................ 422/52; 422/86; 422/93; 436/136
[58] Field of Search ............................ 422/52, 86, 93; 436/136, 177

[56] References Cited

U.S. PATENT DOCUMENTS

| | | | |
|---|---|---|---|
| 3,285,703 | 11/1966 | Narita et al. | 422/52 |
| 3,528,779 | 9/1970 | Fontijn | 422/52 X |
| 4,257,777 | 3/1981 | Dymond et al. | 422/52 X |

OTHER PUBLICATIONS

Mielniczuk, Z. et al. "Photometric Detection of Oxygen" *Anal. Chem.*, 1978, 50, 684–685.
Mielniczuk, Z. M. et al. "Construction and Characteristics of a Cold Flame Photometric Detector" *J. Chromatogr.* 1978, 166, 1–7.
Aue, W. A. et al. "Gas Chromatographic Detector Based on the Quenching of Luminescence from a $P_4/O_2$ Cold Flame" *Can. J. Chem.*, 1979, 57, 1238–1243.
CRC Handbook of Chemistry and Physics Weast, R.C. editor, CRC Press, Inc.: Boca Raton, Fl., 63rd edition, 1982, pp. D-219-D-222.
Stuhl, F. et al. "An Optical Detection Method for NO in the Range of $10^{-2}$ to $10^{-3}$ ppm by the Chemiluminescent Reaction of NO with $O_3$", Technical Report SR 70-42 Ford Motor Company, 1973.
*The Merck Index*, 10th Edition, 1983, pp. 1059–1060.

Primary Examiner—James C. Housel
Assistant Examiner—Arlen Soderquist
Attorney, Agent, or Firm—Lowe, Price, Leblanc & Becker

[57] ABSTRACT

An apparatus for measuring the amount of oxygen in a sample gas, which is suited for quantifying small amount of oxygen in a sample gas. The apparatus of the present invention comprises a yellow phosphorus vapor-providing section in which yellow phosphorus is retained, by which the vapor of the yellow phosphorus is supplied and by which the amount of the vapor of the yellow phosphorus is controlled. The apparatus further comprises a reaction chamber connected to the yellow phosphorus vapor-providing section, in which the light-emitting reaction between the oxygen in the sample and the vapor of the yellow phosphorus is conducted, and a sample gas-supplying section. The amount of the oxygen in the sample gas is determined by measuring the intensity of the light emitted by the reaction by a light intensity-measuring device.

2 Claims, 6 Drawing Sheets

APPARATUS FOR QUANTIFYING OXYGEN

This application is a divisional application of application Ser. No. 07/148,841, filed Jan. 26, 1988, now U.S. Pat. No. 5,021,352.

BACKGROUND OF THE INVENTION

1. Field of the Invention

This invention relates to a method and apparatus for quantifying oxygen contained in a sample gas. The method and apparatus are especially suited for measuring a small amount of oxygen with high accuracy.

II. Background of the Invention

The small amount of oxygen in an industrial gas such as nitrogen, hydrogen, argon and helium is conventionally measured by reacting the oxygen in a sample gas with vapor of yellow phosphorus in a reaction chamber to cause a light-emitting reaction between the oxygen and the vapor of yellow phosphorus. The intensity of the light resulting from the reaction is measured by a photodetector such as photomultiplier tube. The vapor of the yellow phosphorus is obtained by sublimating solid phosphorus at room temperature (15° C. to 25° C.) in the reaction chamber. Since the light intensity of the light emitted by the reaction in the reaction chamber is proportional to the amount of oxygen in the sample gas, the amount of oxygen may be determined by measuring the light intensity of the light emitted by the reaction.

By the conventional method, oxygen may be quantified accurately if the amount of the oxygen is on the order of several ppm to 100 ppm. It is now demanded, however, in the field of, for example, manufacturing of semiconductor devices, that the oxygen in the amount of 1 ppm or less be quantified accurately.

However, the oxygen in the amount of 1 ppm or less may not be quantified accurately since the light intensity is very weak and the photoelectric current supplied from the photodetector is very small accordingly, so that the difference between the intensity of the photoelectric current supplied from the photodetector and the dark current of the photodetector (electric current supplied from the photodetector in the absolute absence of light) becomes small.

Thus, a method by which oxygen in the amount of 1 ppm or less may be quantified accurately is needed.

SUMMARY OF THE INVENTION

Accordingly, the object of the present invention is to provide a method and an apparatus for quantifying oxygen in a sample gas by which a small amount of oxygen on the order of 1 ppm or less may accurately be quantified.

The present inventors have found that if the reaction between the oxygen contained in a sample gas in a small amount and the vapor of yellow phosphorus is conducted under a vapor pressure of the yellow phosphorus which is lower than the saturated vapor pressure of the yellow phosphorus at room temperature, the photoelectric current supplied from the photodetector is increased, so that the difference between the intensity of the photoelectric current supplied from the photodetector and the dark current thereof is made large, thus the quantification of the oxygen may be made accurately. That is, although the light intensity of the reaction in the reaction chamber is the same as in the case where the reaction is conducted at the saturated vapor pressure of the yellow phosphorus at the room temperature, as long as the amount of the yellow phosphorus vapor is not less than the stoichiometrical amount, the lower the vapor pressure of the yellow phosphorus, the greater the photoelectric current supplied from the photodetector. It has been recognized by those skilled in the art, when the amount of oxygen in a sample gas is very small, the vapor of yellow phosphorus obtained by sublimating the yellow phosphorus at room temperature is in excess of the stoichiometric amount. It has long been believed by those skilled in the art, however, since the oxygen in the sample gas is completely reacted with the yellow phosphorus vapor, the light intensity of the light-emitting reaction in the reaction chamber (original light intensity) is constant irrespective of the amount of the yellow phosphorus, so that the light intensity measured by the photodetector (measured light intensify) is also constant irrespective of the amount of the yellow phosphorus vapor. However, in actuality, as mentioned above, even if the original light intensity in the reaction chamber is the same, the smaller the amount of the yellow phosphorus vapor, the larger the measured light intensity measured by the photodetector. The present invention is based on this very surprising and totally unexpected finding.

Thus, the present invention provides a method of quantifying oxygen in a sample gas comprising reacting the oxygen and vapor of yellow phosphorus under a vapor pressure of the yellow phosphorus which is lower than the saturated vapor pressure of the yellow phosphorus at room temperature; and measuring the intensity of light emitted by the reaction.

The present invention further provides an apparatus for quantifying oxygen in a sample gas comprising a yellow phosphorus vapor-providing section including means for retaining yellow phosphorus, means for supplying the vapor of the yellow phosphorus, and means for controlling the amount of the vapor supplied; a reaction chamber connected to the yellow phosphorus vapor-providing section, in which light-emitting reaction between the oxygen in the sample and the vapor of the yellow phosphorus is conducted; a sample gas-supplying section including means for supplying a sample gas to the reaction chamber and means for controlling the amount of the sample gas supplied; and means for measuring the intensity of the light emitted by the light-emitting reaction.

By the present invention, although the range of the oxygen level in which the oxygen may be quantified accurately by the conventional method may also be measured accurately, low levels of oxygen of 1 ppm or less, which is difficult to quantify by the conventional method, may be quantified accurately.

DETAILED DESCRIPTION OF THE PREFERRED EMBODIMENTS

In the method of the present invention, the oxygen contained in a sample gas is reacted with yellow phosphorus vapor in a reaction chamber Upon contact with vapor of yellow phosphorus, oxygen autogenically reacts therewith to emit light. Since the intensity of the light emitted by the reaction is proportional to the amount of oxygen contained in the sample gas, the oxygen in the sample gas may be quantified by measuring the intensity of the light. Measurement of the light may be conducted by using light-intensity measuring means such as a photomultiplier tube as in the prior art.

The vapor of yellow phosphorus may be obtained by sublimating solid yellow phosphorus. Unlike the prior art method wherein the sublimation of the yellow phosphorus is conducted in the reaction chamber at room temperature (15° C. to 25° C.)(i.e., the vapor pressure of the yellow phosphorus in the reaction chamber is the saturated vapor pressure of the yellow phosphorus at room temperature), in this invention, the vapor pressure of the yellow phosphorus vapor in the reaction chamber is lower than the saturated vapor pressure of yellow phosphorus vapor at room temperature. As is well-known, the amount of the yellow phosphorus is proportional to the vapor pressure of the yellow phosphorus. Thus, in the present invention, oxygen is reacted with an amount of yellow phosphorus which is smaller than in the conventional method. By this, low levels of oxygen, i.e., 1 ppm or less may accurately be quantified.

The reduction of the vapor pressure of the yellow phosphorus vapor in the reaction chamber may be conveniently conducted by simply cooling the solid yellow phosphorus placed in the reaction chamber to a temperature lower than room temperature. As is well-known, the lower the temperature, the smaller the yellow phosphorus vapor obtained from solid yellow phosphorus.

Alternatively, solid yellow phosphorus may be retained in a gas tight container connected to the reaction chamber via a duct and the vapor from the solid yellow phosphorus may be carried by a carrier gas, and the reduction of the vapor pressure of the yellow phosphorus vapor in the reaction chamber may be conducted by controlling the flow rate of the carrier gas and/or the temperature of the solid yellow phosphorus. The carrier gas should be inert with respect to the yellow phosphorus vapor and should not contain a substantial amount of oxygen. Examples of the carrier gas may include inert gases such as nitrogen, argon and helium, as well as hydrogen If the carrier gas contains oxygen, the carrier gas should be used after deoxidization.

The actual operation parameters such as the temperature of the solid yellow phosphorus and/or the flow rate of the carrier gas may be determined routinely by preparing a calibration curve as hereinafter described in detail.

The apparatus of the invention will now be described with reference to the drawings.

Figure 1:
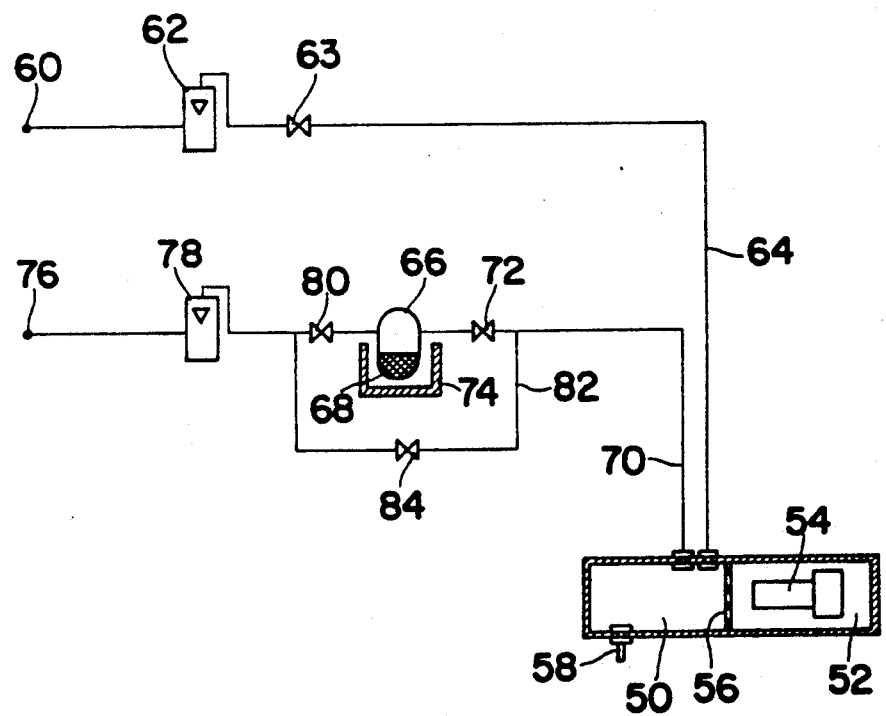
FIGS. 1 to 3 each shows an embodiment according to the present invention wherein the solid yellow phosphorus is contained in a gas tight container which is separated from the reaction chamber.

FIG. 1 is a schematic view showing an embodiment of an apparatus according to the present invention. The apparatus shown in FIG. 1 comprises a reaction chamber 50 in which the reaction between the oxygen in the sample gas and yellow phosphorus vapor is conducted. Adjacent to the reaction chamber 50, is provided a measuring chamber 52 in which light intensity-measuring means such as a photomultiplier tube 54 is placed. The reaction chamber 50 and the measuring chamber 52 are separated by a transparent plate 56 made of e.g., an optical glass. A discharge duct 58 is connected to the reaction chamber 50, through which the exhausted gas is discharged. Also connected is a sample gas supplier 60 via a sample gas-supplying duct 64 in which a sample gas flowmeter 62 and a sample gas inlet valve 63 are provided.

A gas tight container 66 in which solid yellow phosphorus 68 is contained is connected to the reaction chamber 50 via a carrier gas-supplying duct 70. An outlet valve 72 is provided in the carrier gas-supplying duct 70 between the container 66 and the reaction chamber 50. The container 66 is placed in a thermostatic bath 74. The container 66 is connected to a carrier gas-introducing section 76 via a flowmeter 78 and an inlet valve 80. The degree of opening of the inlet valve 80 and/or the outlet valve 72 is manually controlled while reading the flowmeter 78 to control the flow rate of the carrier gas. A bypass 82 is branched off from the carrier gas-supplying duct 70, and bypasses the inlet valve 80, container 66 and the outlet valve 72. The bypass 82 has a valve 84.

The term "thermostatic bath" herein used includes any means which can keep the temperature of the container 66, and in turn, the temperature of the solid yellow phosphorus 68 at a temperature lower than room temperature. The thermostatic bath includes means by which the temperature of the container 66 is changed and means by which the temperature of the container cannot be changed. An example of the former means may include those in which a coolant flows and the flow rate of the coolant may be controlled (such as a refrigerator). The temperature of this type of thermostatic bath may be changed by changing the flow rate of the coolant. An example of the latter means may include an iced water bath and a dry ice bath. In this case, the temperature of the container is kept at the temperature of the iced water or the dry ice.

Figure 3:
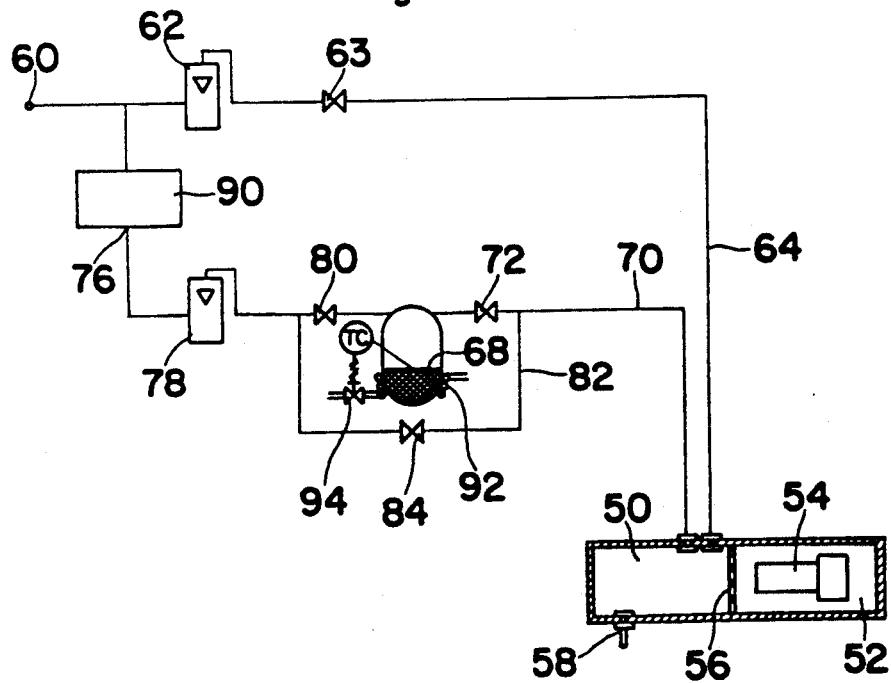

As an alternative to the thermostatic bath, a cooling tube may be wound about the container 66 through which a coolant flows (see FIG. 3). With this arrangement, the temperature of the container 66 may be controllably changed by controlling the flow rate of the coolant which flows in the cooling tube. It should be noted, however, as mentioned above, the control of the amount of the yellow phosphorus vapor supplied to the reaction chamber 50 may also be conducted by controlling the flow rate of the carrier gas.

In operation, firstly, with closing the valves 80 and 72 and opening the valve 84, carrier gas is supplied to the reaction chamber 50 via the bypass 82 of the carrier gas-supplying duct 70 to purge the reaction chamber 50. Then the valve 63 is opened to a controlled degree of opening, and the sample gas is supplied to the reaction chamber 50 via the sample gas supplying duct 64. While keeping the temperature of the thermostatic bath 74 at a prescribed temperature, the valve 84 is closed and the valves 80 and 72 are opened (valve 80 is opened to a controlled degree of opening), and carrier gas accompanying the yellow phosphorus vapor obtained by the sublimation of the solid yellow phosphorus 68 is supplied to the reaction chamber 50 via the carrier gas-supplying duct 70. By the above-mentioned operation, in the reaction chamber 50, the oxygen contained in the sample gas reacts with the yellow phosphorus vapor in the carrier gas to emit light and the light intensity is measured by the photomultiplier tube 54 to output a photoelectric current. The intensity of the resulting photoelectric current supplied from the photomultiplier 54 is compared with a calibration curve preliminarily prepared in the same conditions to indicate the oxygen level in the sample gas. As is discovered by the present inventors, as long as the oxygen contained in the sample gas is completely reacted, the smaller the amount of the yellow phosphorus vapor in the reaction chamber 50, the stronger the measured light intensity of the reaction between the oxygen and the yellow phosphorus vapor which is measured by the photomultiplier 54. Therefore, by bringing the photoelectric current supplied from the photomultiplier tube 54 to a peak or the vicinity thereof by controlling the amount of the yellow phosphorus vapor supplied to the reaction chamber 50 by controlling the temperature of the thermostatic bath and/or the flow rate of the carrier gas accompanying the yellow phosphorus vapor, and by preparing the calibration curve while maintaining the conditions, the oxygen level in the sample gas may be determined with high accuracy. Alternatively, calibration curves are preliminarily prepared under varying amounts of yellow phosphorus vapor, and the optimum amount of the yellow phosphorus vapor is determined as mentioned above. Using the calibration curve prepared using the optimum amount or the amount which is close thereto of the yellow phosphorus vapor, the oxygen level may be measured employing the same conditions in which the selected calibration curve is prepared. It should be noted that in cases where the temperature of the thermostatic bath 74 is kept constant, the calibration curve is prepared while controlling the amount of the yellow phosphorus vapor by controlling the flow rate of the carrier gas. In this case, although the calibration curve may be prepared without the flowmeter 78 for the carrier gas, that is, without measuring the flow rate of the carrier gas, needless to say, it is more convenient to provide the flowmeter 78 for the preparation of the calibration curve and for the measurement of the oxygen in the sample gas.

Figure 2:
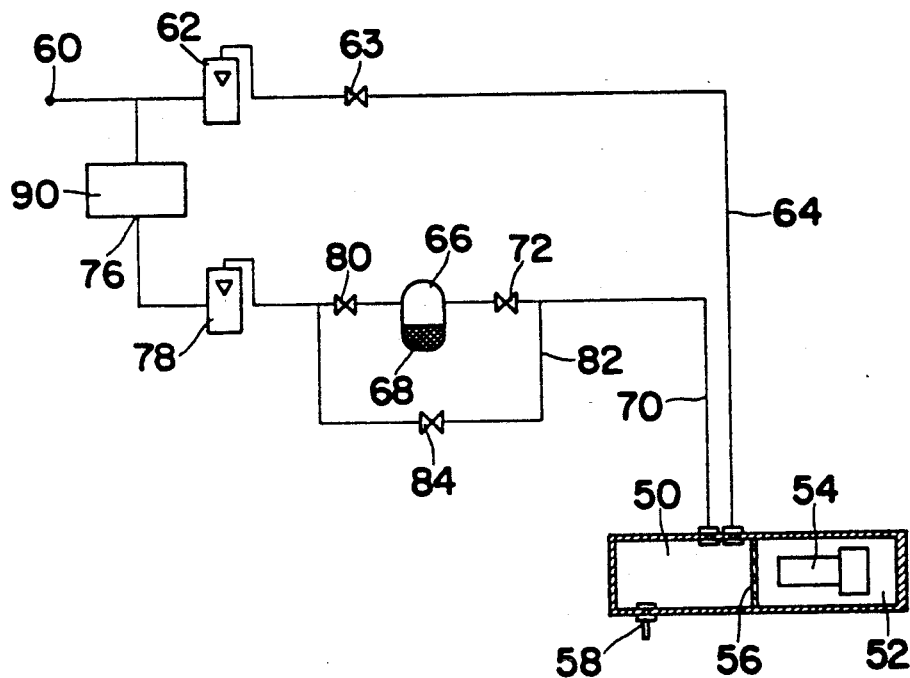

FIG. 2 shows another embodiment of the apparatus of the present invention. In this embodiment, the carrier gas-introducing section 76 is connected to the sample gas-supplying duct 64 via a deoxidizer 90. With this embodiment, the sample gas is co-used as the carrier gas after deoxidization by the deoxidizer 90. The apparatus of this embodiment has an advantage in that the separate carrier gas-introducing section may be omitted. The apparatus of the embodiment shown in FIG. 2 does not have a thermostatic bath and the amount of the yellow phosphorus vapor may be controlled by controlling the flow rate of the carrier gas by controlling the degree of opening of the valve 80 and/or the valve 72.

FIG. 3 shows still another embodiment of the apparatus of the present invention. In this embodiment, the control of the temperature of the solid yellow phosphorus is conducted by the combination of a cooling tube 92 wound about the container 66, a coolant inlet valve 94 provided in the tube 92, and a temperature controller (designated as "TC" in FIG. 3) which measures the temperature of the yellow phosphorus 68 and is functionally connected to the valve 94. With the apparatus of this embodiment, the amount of the phosphorus vapor may be controlled by controlling the temperature of the container 66 by controlling the flow rate of the coolant flowing in the cooling tube 92.

Other embodiments of the apparatus of the present invention wherein the solid phosphorus is placed in the reaction chamber will now be described referring to FIGS. 4 to 6.

Figure 4:
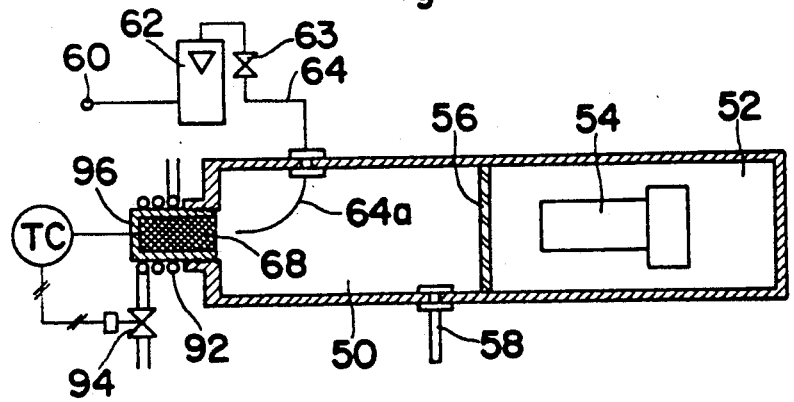
FIGS. 4 to 6 each shows another type of embodiment according to the present invention wherein the solid yellow phosphorus is contained in the reaction chamber.

In the embodiment shown in FIG. 4, a container 96 with an opening is mounted on the reaction chamber 50 such that the opening faces and communicates to the inside of the reaction chamber 50. Solid phosphorus 68 is contained in the container 96. The tip 64a of the sample gas supplying duct 64 is extended in the reaction chamber 50 to the vicinity of the opening of the container 96 in the reaction chamber 50. This structure is advantageous when the container 96 is removed for supplementing the solid yellow phosphorus because an inert gas may be jetted from the tip 64a so as to prevent the solid yellow phosphorus from drastically reacting with the oxygen in the air. In this embodiment, as in the embodiment shown in FIG. 3, a cooling tube 92 is wound about the container 96 in which a coolant flows, and a valve 94 and a temperature controller are provided as explained referring to FIG. 3. With this embodiment, the vapor pressure of the yellow phosphorus vapor may be controlled by cooling the container 96 by passing the coolant through the cooling tube 92.

Figure 5:
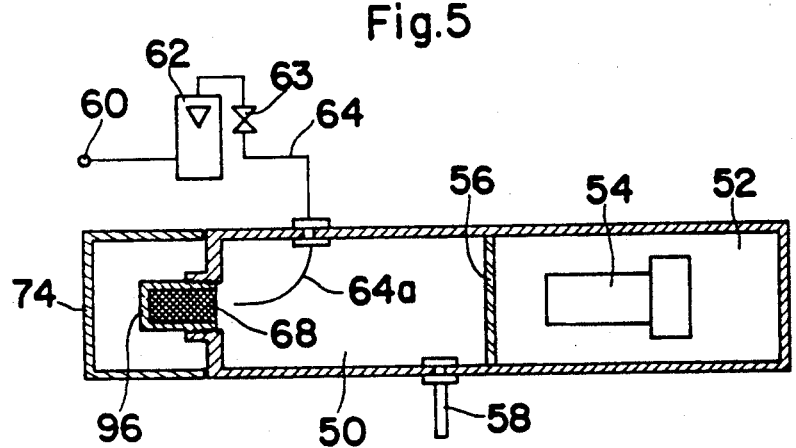

Alternatively, as shown in FIG. 5, the container 96 may be placed in a thermostatic bath 74. Alternatively, as shown in FIG. 6, the entire apparatus may be contained in a thermostatic bath 74. In this case, although the photomultiplier tube 54 in the measuring chamber 52 is also cooled, this is preferable because, in general, the photomultiplier tube 54 operates better at a low temperature.

Figure 6:
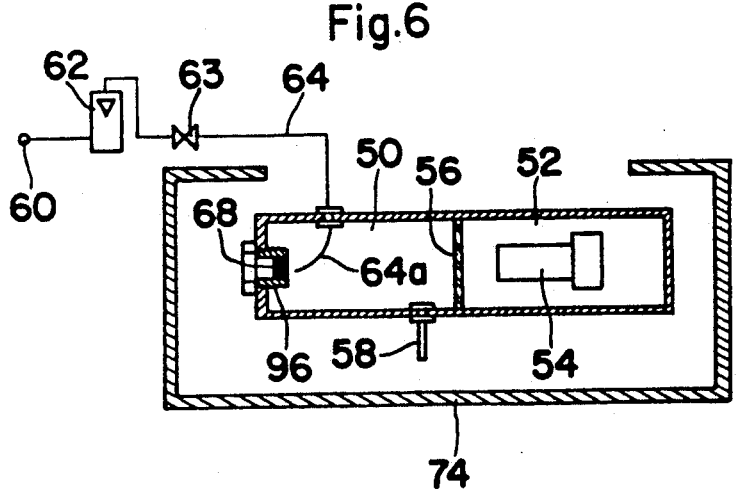

The embodiments shown in FIGS. 4 to 6 have an advantage that they are easily manufactured by slightly modifying the apparatus which is conventionally used. That is, since the embodiments shown in FIGS. 4 to 6 differ from the conventional apparatus in that they have means for cooling the temperature of the solid phosphorus contained in the container, they are easily manufactured by providing the cooling means to the conventional apparatus.

EXAMPLE 1

Using an apparatus of the embodiment shown in FIG. 1, the following operation was conducted:

The valves 80 and 72 were closed and the valve 84 was opened, and a carrier gas was supplied to the reaction chamber 50 to purge the same via the bypass 82. Then the valve 63 was controllably opened and a reference gas containing 1 ppm of oxygen was supplied via the sample gas supplying duct 64 to the reaction chamber 50 at a flow rate of 500 ml/min. In these conditions, the dark current $I_o$ from the photomultiplier tube 54 was measured. The dark current $I_o$ measurement was repeated over the range of temperatures set forth in FIG. 7.

Then the valve 84 was closed and the valves 80 and 72 were opened. By controlling the degree of opening of the valve 80, the flow rate of the carrier gas accompanying the yellow phosphorus vapor was set to 10 ml/min, and the carrier gas was introduced into the reaction chamber 50. The temperature T of the thermostatic bath 74 was changed from +25° C. to −5° C. at intervals of 5° C. At each temperature, the intensity I of the photoelectric current supplied from the photomultiplier tube 54 was recorded. The relationship between the T and the I is shown in FIG. 7.

Figure 7:
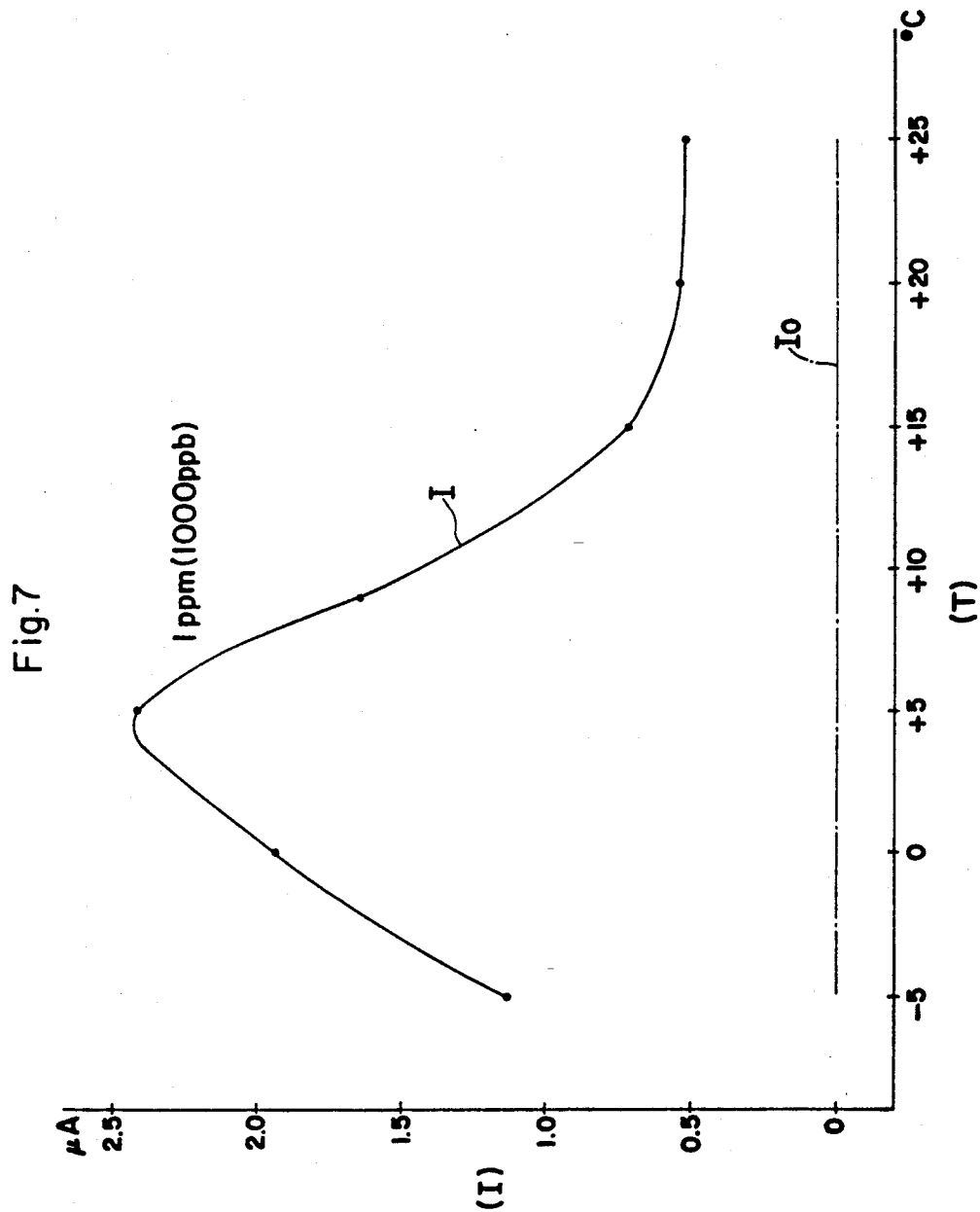
FIG. 7 shows the relationship between the intensity of the measured photoelectric current supplied from a photomultiplier tube and the temperature of the thermostatic bath.

As is seen from FIG. 7, irrespective of the temperature T, the value of the dark current $I_o$ is substantially the same. When the temperature T is at room temperature, i.e., from 15° C. to 25° C. (this is the case in the conventional method wherein the temperature of the solid yellow phosphorus is not controlled and the measurement is conducted at room temperature), the intensity I is small and the difference between the intensity I and that of the dark current $I_o$ is also small accordingly. By lowering the temperature T to a temperature lower than room temperature, the intensity I becomes great and the difference of the intensity I and that of the dark current $I_o$ is also becomes large accordingly. As shown in FIG. 7, the intensity I has a peak at +5° C., so that the measurement of the amount of the oxygen gas contained in the sample gas may most accurately be determined employing this temperature, if the oxygen level to be determined is around 1 ppm.

Figure 8:
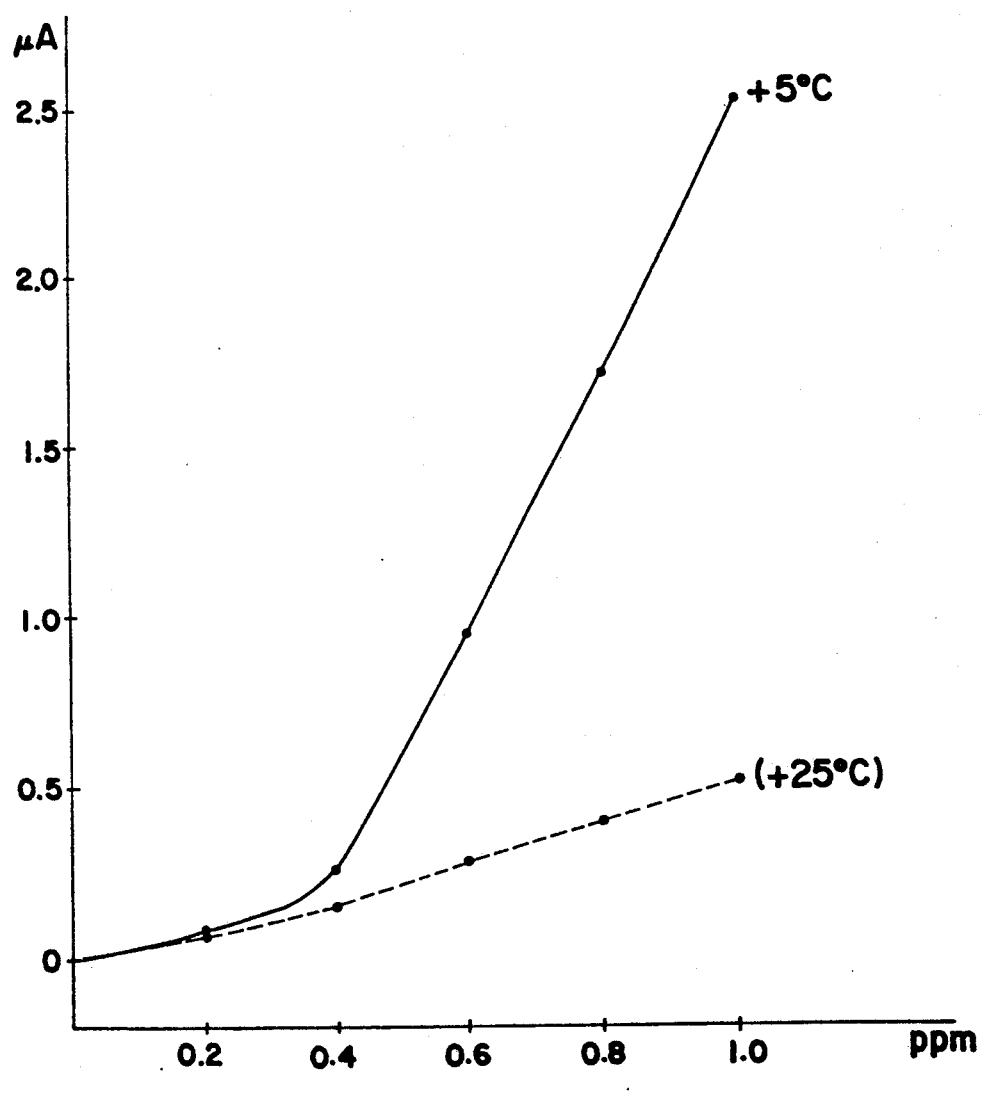
FIG. 8 shows a calibration curve prepared according to the method of the present invention.

Thus, setting the temperature of the thermostatic bath at +5° C., reference gases each containing oxygen in the amount of 0.2 ppm, 0.4 ppm, 0.6 ppm or 0.8 ppm were supplied serially to the reaction chamber 50 via the sample gas supplying duct 64 in the same conditions as mentioned above. For each reference gas, the intensity of the photoelectric current supplied from the photomultiplier tube 54 was recorded and was plotted with respect to the concentration of the oxygen in the sample gas to obtain a calibration curve shown in FIG. 8. For comparison, a calibration curve was prepared employing a temperature of the thermostatic bath of +25° C., which calibration curve is shown in FIG. 8 as a broken line. By comparing the calibration curves obtained at +5° C. and +25° C., it is seen that the slope of the curve is steeper in the curve at +5° C. than that at +25° C., so that the accuracy of the measurement is higher in the measurement employing the temperature of +5° C. than that employing the temperature of +25°C.

EXAMPLE 2

The same procedure as in example 1 was repeated except that the reference gas contained oxygen in the amount of 100 ppb, 80 ppb, 60 ppb or 40 ppb, the flow rate of the carrier gas was set to 2 ml/min., and the temperature of the thermostatic bath was from +20° C. to −20° C. to obtain curves similar to the curve shown in FIG. 7.

Figure 9:
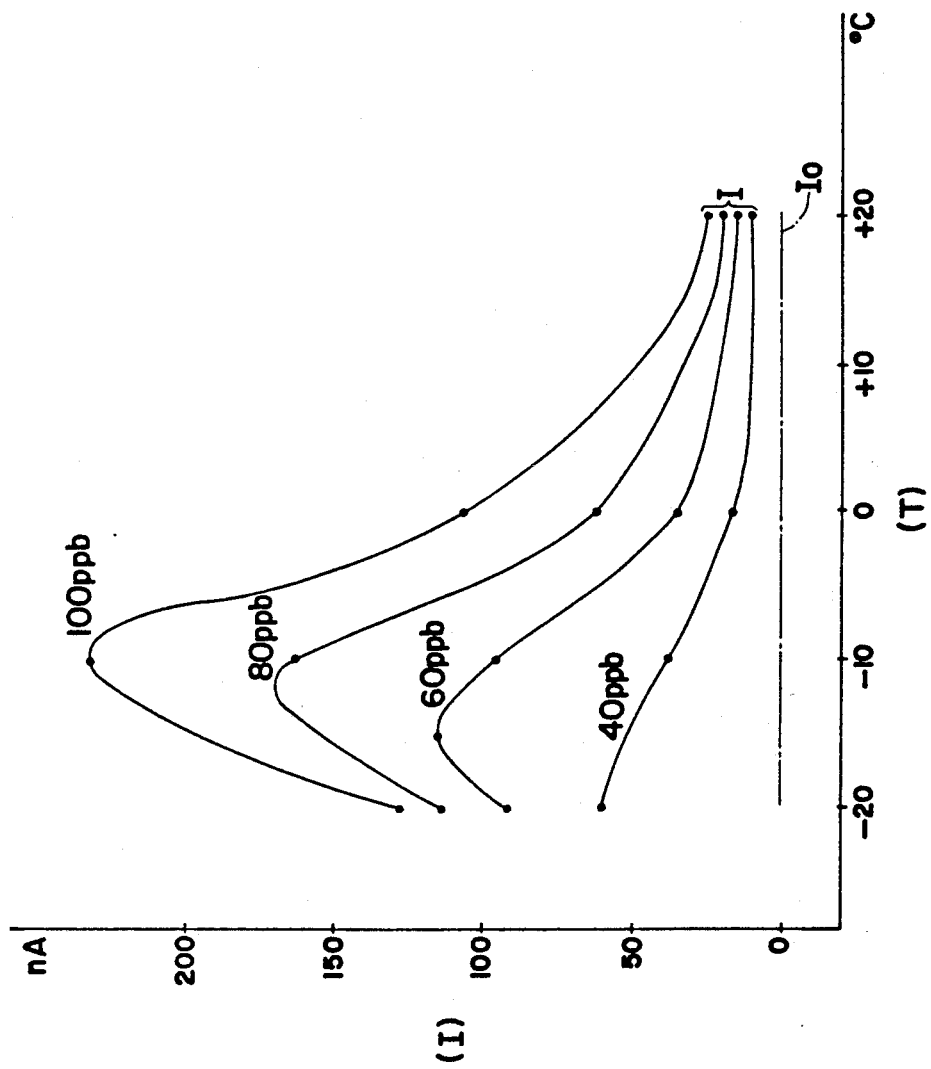
FIG. 9 shows the relationship between the intensity of the measured photoelectric current supplied from the photomultiplier tube and the temperature of the thermostatic bath for reference gases containing varying amounts of oxygen.

The curves are shown in FIG. 9. Similar to the curve shown in FIG. 7, the curves obtained for the reference gas containing oxygen in the amount of 100 ppb, 80 ppb and 60 ppb have a peak at a temperature lower than a room temperature. Although the clear peak does not exist in the curve for the reference gas containing 40 ppb of oxygen, it is believed that a peak will emerge at a temperature lower than −20° C., or the peak may be obtained by reducing the carrier gas flow rate. Any way, even for the reference gas containing 40 ppb of oxygen, the intensity of the measured photoelectric current supplied from the photomultiplier tube 54 is greater at the temperature which is lower than room temperature. Thus, oxygen contained in the sample gas an the order of as small as 100 ppb or less may be accurately quantified by setting the temperature of the thermostatic bath to a temperature lower than the room temperature.

Although the invention was described referring to a specific embodiment thereof, it is apparent for those skilled in the art that many modifications may be made without departing from the spirit and scope of the present invention. For example, in the above-mentioned embodiments, the flowmeter 78 may be replaced with a flow indicating controller and the flow rate of the carrier gas may be controlled by controlling the degree of opening of the valve disposed in the flow indicating controller. Similarly, the flowmeter 62 may be replaced with a flow indicating controller and the flow rate of the sample gas may be controlled by controlling the degree of opening of the valve disposed in the flow indicating controller. Thus, the above description should not be construed restrictively.

We claim:
1. An apparatus for quantifying oxygen in a sample gas comprising:
   a reaction chamber in which light-emitting reaction between oxygen in a sample gas and vapor of yellow phosphorus is conducted;
   means for measuring the intensity of the light emitted by said light-emitting reaction;
   means for supplying a desired amount of said sample gas to said reaction chamber;
   a gas-tight yellow phosphorus container for retaining said yellow phosphorus, said yellow phosphorus container being provided separately from said reaction chamber;
   means for supplying yellow phosphorus vapor from said yellow phosphorus container, together with a carrier gas, to said reaction chamber; and
   means for cooling said yellow phosphorus container such that said yellow phosphorus in said yellow phosphorus container is cooled to a temperature lower than room temperature.

2. An apparatus for quantifying oxygen in a sample gas comprising:
   a reaction chamber in which light-emitting reaction between oxygen in the sample gas and vapor of yellow phosphorus is conducted;
   means for measuring the intensity of the light emitted by said light-emitting reaction;
   means for supplying a desired amount of said sample gas to said reaction chamber;
   a yellow phosphorus container for retaining said yellow phosphorus, which container is integral with and has an opening, in communication with said reaction chamber; and
   means for cooling said yellow phosphorus container such that said yellow phosphorus in said yellow phosphorus container is cooled to a temperature lower than room temperature.

* * * * *